(12) United States Patent
Grigg et al.

(10) Patent No.: US 7,714,115 B2
(45) Date of Patent: May 11, 2010

(54) METHOD OF DEPROTECTION

(75) Inventors: Julian Grigg, Amersham (GB); Nigel Osborn, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 377 days.

(21) Appl. No.: 11/576,625

(22) PCT Filed: Sep. 23, 2005

(86) PCT No.: PCT/GB2005/003692

§ 371 (c)(1),
(2), (4) Date: Apr. 4, 2007

(87) PCT Pub. No.: WO2006/037950

PCT Pub. Date: Apr. 13, 2006

(65) Prior Publication Data

US 2008/0076914 A1    Mar. 27, 2008

(30) Foreign Application Priority Data

Oct. 5, 2004    (GB) ................................ 0422004.2

(51) Int. Cl.
*C07H 1/00*    (2006.01)
(52) U.S. Cl. .................................... 536/18.4
(58) Field of Classification Search ........................ None
See application file for complete search history.

(56) References Cited

U.S. PATENT DOCUMENTS

| 5,135,683 | A  | 8/1992 | Cooper |
| 6,172,207 | B1 | 1/2001 | Damhaut et al. |
| 6,184,309 | B1 | 2/2001 | Schwindeman et al. |
| 2004/0110720 | A1 | 6/2004 | Martin |
| 2005/0137421 | A1 | 6/2005 | Walsh et al. |

FOREIGN PATENT DOCUMENTS

| WO | 94/00460 | 1/1994 |
| WO | 03/090789 | 11/2003 |

OTHER PUBLICATIONS

Encarta's Online Dictionary "protecting group"—available at http://encarta.msn.com/encnet/features/dictionary/DictionaryResults.aspx?refid=561533921, last viewed Jul. 30, 2009.*
GB0422004.2 Search Report dated Jan. 12, 2005.
PCT/GB2005/003692 International Search Report and Written Opinion dated Jan. 19, 2006.
Li, B, et.al., "Aqueous phosphoric acid as a mild reagent for deprotection of the t-butoxycarbonyl group" Tetrahedron Letters, Elsevier, Amersterdam, NL vol. 44, No. 44, Oct. 27, 2003, pp. 8113-8115.
Hamacher, K, et.al. "Efficient stereospecific synthesis of no-carrier-added 2- 18F-Fluoro-2-deoxy-D-glucose using aminopolyether supported nucleophilic substitution" Journal of Nuclear Meeicine, Society of Nuclear Medicine, Reston, VA, vol. 27, No. 2, Feb. 1, 2986 pp. 235-238.
Yu-Shin Ding, et.al. "Synthesis of high specific activity 6-18F-fluorodopamine for positron emission tomography studies of sympathetic nervous tissue" J. Med. Chem., No. 34, 1991, pp. 861-863.

* cited by examiner

*Primary Examiner*—Shaojia Anna Jiang
*Assistant Examiner*—Bahar Schmidtmann
(74) *Attorney, Agent, or Firm*—Craig Bohlken

(57) ABSTRACT

The invention provides a method for the synthesis of an 18F-labelled product comprising deprotected of a protected 18F-labelled compound using a deprotection agent comprising a weak acid and wherein neutralisation and buffering of the deprotected product are carried out by the addition of a neutralisation agent. The deprotected product is buffered in a pH range suitable for subsequent autoclaving and formulation into an injectable radiopharmaceutical.

24 Claims, 1 Drawing Sheet

METHOD OF DEPROTECTION

This application is a filing under 35 U.S.C. 371 of international application number PCT/GB2005/003692, filed Sep. 23, 2005, which claims priority to application number 0422004.2 filed Oct. 5, 2004, in Great Britain the entire disclosure of which is hereby incorporated by reference.

TECHNICAL FIELD OF THE INVENTION

The present invention relates to the field of radiosynthesis, and more specifically to the synthesis of $^{18}$F-labelled compounds which may be suitable for use as positron emission tomography (PET) tracers.

DESCRIPTION OF RELATED ART

The favoured radioisotope for PET, $^{18}$F, has a relatively short half-life of approximately 110 minutes. $^{18}$F-labelled tracers for PET therefore have to be synthesised and purified as rapidly as possible, the whole process ideally taking less than 1 hour. Standard synthetic methods for introducing $^{18}$F can be relatively slow and may require post-reaction purification (for example, by HPLC) which means that it is difficult to obtain the $^{18}$F-labelled tracer for clinical use in good radiochemical yield. An outline of the main steps in a typical synthetic route for an $^{18}$F tracer is illustrated in FIG. 1.

It would be advantageous to shorten the time taken to complete any of these steps in order to increase the non-corrected radiochemical yield of the final product. A yield increase of 0.6% is obtained for each minute by which the synthesis time is shortened. $^{18}$F-labelled compounds are typically synthesised by radiofluorinating a suitable precursor compound using the [$^{18}$F]-fluoride ion ($^{18}$F$^-$), which is normally obtained as an aqueous solution from the nuclear reaction $^{18}$O(p,n)$^{18}$F and is made reactive by the addition of a cationic counterion and the subsequent removal of water. The precursor compounds are normally selectively chemically protected so that radiofluorination takes place at a particular site on the compound. Following the radiofluorination reaction, the protected $^{18}$F-labelled compound is deprotected in order to yield the desired $^{18}$F-labelled compound. A variety of agents are known to be useful as protecting groups, and suitable protection and deprotection methodologies may be found, for example, in "Protecting Groups in Organic Synthesis", Theodora W. Greene and Peter G. M. Wuts, published by John Wiley & Sons Inc.

Amongst the $^{18}$F-labelled compounds suitable for use as PET tracers [$^{18}$F]-fluorodeoxyglucose ([$^{18}$F]-FDG) is a well-known example. [$^{18}$F]-FDG can be synthesised in a reaction of the protected precursor compound tetraacetylated D-mannose with $^{18}$F$^-$ [Hamacher et al 1986 J. Nucl. Med. 27(2) pp 235-8]. The protected $^{18}$F-labelled compound can be subsequently deprotected by acid hydrolysis, for example using hydrochloric acid, followed by neutralisation with a base such as sodium hydroxide, for example at 2M concentration. This process has to be conducted with care, however, as in some cases the $^{18}$F in the labelled compound is replaced by Cl, especially where the deprotection is performed in hydrochloric acid. It is therefore preferable to conduct the reaction at a low temperature, preferably room temperature or below.

An alternative method for deprotection is to use base hydrolysis, for example with sodium hydroxide, followed by neutralisation with an acid, typically hydrochloric acid.

Similar protection/deprotection and buffering methodologies are used in the synthesis of other known $^{18}$F-labelled compounds.

The use of weak acids as deprotecting agents is known in the art. U.S. Pat. No. 6,184,309 describes a process for removing protecting groups from polymers using acid catalysis, wherein a number of strong and weak organic and inorganic acids are suggested as deprotecting agents. Among the large number of acids mentioned are phosphoric acid and acetic acid. US 2003/0212249 reports the synthesis of cyclosporine analogues wherein a trimethylsilyl protecting group can be removed using acetic acid or citric acid. U.S. Pat. No. 5,135,683 relates to the preparation of deprotected polyols, suggesting phosphoric acid as an agent for the removal of cyclic ketal protecting groups. Li et al [2003 Tetrahedron Letters 44 pp 8113-5] report the use of 85 wt% aqueous phosphoric acid for the acid hydrolysis of t-butoxycarbonyl-protected amines. In this reaction, aqueous phosphoric acid (85 wt%) was added to a solution of the protected amine in an organic solvent. Water was added to dilute the reaction mixture and then an aqueous solution of sodium hydroxide was added to adjust the pH to 7.8. The sodium phosphate formed in the workup was said to act as a buffer to prevent the pH rising above this level. Interestingly, the document teaches that, although amines were successfully deprotected under the conditions used, benzyl and methyl esters survived the reaction conditions. None of these documents teaches use of a weak acid for deprotection in the synthesis of an $^{18}$F-labelled compound.

The reaction for the preparation of an $^{18}$F-labelled compound is conveniently carried out as an automated synthesis in which the reagents are present in cassette form and in which syringe drivers may be used to control the dispensing of the acid and the neutralising agent. The respective errors in dispensing the acid and the neutralising agent where syringe drivers are used can be as great as 10% (1 ml+/−0.1 ml). The final pH of the solution of the $^{18}$F-labelled compound must be maintained between 4.5 and 6.5 prior to sterilisation, otherwise the radiochemical purity of the sterilised product may be compromised (FDM is produced from the Lobry de Bruyn-van Eckenstein rearrangement of FDG forming FDM). There are also significant errors in the formulation of the acid and base, typically in the order of 1% for each concentration Therefore, the presence of a buffer is required to ensure that the ultimate pH remains within the desired range in spite of the dispensing errors. A phosphate buffer is typically used for buffering the product prior to sterilisation, addition of the buffer being conveniently carried out at the same time as neutralisation by means of a solution of the neutralising agent (for example NaOH) in a buffer solution. However, it has been found this can also present problems as phosphate is not very soluble in basic solutions and tends to precipitate out, especially at low temperatures. An investigation was carried out by the present inventors into the introduction of phosphate buffer for maintaining the pH of a neutralised acid solution in an automated process. This involved examining a number of concentrations of sodium phosphate in 2M NaOH at 2° C., as it was desired to know whether cassettes containing this reagent could feasibly be transported at low temperatures. Sodium phosphate was observed to precipitate out of solution at concentrations above around 40 mg/ml, precluding the formulation having sufficient buffering capacity to cope with the relatively large error in the dispensing volumes.

SUMMARY OF THE INVENTION

The invention provides a method for the synthesis of an $^{18}$F-labelled product wherein neutralisation and buffering of the deprotected product are carried out by the addition of a neutralisation agent. The deprotected product is buffered to a pH range suitable for subsequent autoclaving and formulation into an injectable radiopharmaceutical.

DETAILED DESCRIPTION OF THE INVENTION

In a first aspect, the present invention provides a method for the synthesis of an $^{18}$F-labelled compound, comprising the following steps:

(i) deprotection of a protected $^{18}$F-labelled compound corresponding to the $^{18}$F-labelled compound using a deprotection agent comprising a weak acid; and, (ii) neutralisation and buffering of the product of step (i) by addition of a neutralisation agent, wherein buffering is between pH 4.5 and 8.0.

The process of the invention provides advantages over the prior art. There is no need for the use of a separate buffer solution in an automated process to account for error in the amount of reagent dispensed by a syringe driver. The pH of the product solution will be maintained within acceptable limits by virtue of the buffering characteristics of the weak acid once the neutralisation agent has been added.

The method of the invention also overcomes the problems which are encountered when deprotection is carried out with a strong acid such as hydrochloric acid, and a buffer is added with the neutralising agent. Since the buffer is formed from the weak acid used in the deprotecting step combined with the neutralisation agent, it is not necessary to dissolve the buffer forming compound in the basic neutralising agent and there will consequently be no solubility problems arising from this.

In order to further describe the invention a number of terms are defined as follows:

A compound is regarded as "$^{18}$F-labelled" when at least one $^{18}$F atom has been chemically introduced into the compound. Typically, the $^{18}$F atom in the $^{18}$F-labelled compound is covalently bound to the compound.

In the context of the present invention, a "protected $^{18}$F-labelled compound" is a chemically protected intermediate in the synthesis of the $^{18}$F-labelled compound resulting from radiofluorination of a suitable protected precursor compound. The protecting group of the protected $^{18}$F-labelled compound is susceptible to removal by acid hydrolysis and deprotection yields the final $^{18}$F-labelled compound. Typically, the protected $^{18}$F-labelled compound has one or more protected groups chosen from hydroxyl (which may form part of a carboxylic acid moiety) and amine groups. Suitable protecting groups for these moieties are well known in the art and are described, for example in "Protecting Groups in Organic Synthesis", Theodora W. Greene and Peter G. M. Wuts, published by John Wiley & Sons, Inc.

The term "weak acid" is a term known in the art, and means an acid that partially dissociates in an aqueous solution. In the context of the present invention, a weak acid is an acid having a pKa of 2 or more.

The term "neutralisation agent" in the context of the present invention is taken to mean an agent that is sufficiently basic to bring the pH of the deprotected solution to the desired pH range of 4.5 to 8.0. Examples of suitable neutralisation agents of the present invention include inorganic hydroxides, inorganic oxides and inorganic salts of weak acids. Inorganic hydroxides are preferred neutralisation agents of the invention, with NaOH and KOH being especially preferred.

It is greatly preferred that the method of the invention is carried out under mild conditions, and at a temperature of from 10 to 50° C. and most preferably at room temperature, although much higher temperatures can be used if necessary, for example up to 145° C. The protecting group will therefore need to be chosen such that it can be removed by acid hydrolysis under the chosen reaction conditions. A person of skill in the art would have no difficulty in selecting a suitable protecting group.

The protected $^{18}$F-labelled compound may be any protected compound, for example an amine, a hydroxy compound or a carboxylic acid and the protecting group to be removed in the deprotection step (a) will be chosen accordingly. It is, of course, essential that the protecting group of the protected $^{18}$F-labelled compound is susceptible to removal by acid hydrolysis.

Protecting groups are well known in the art and detailed information on protecting groups can be found, for example, in "Protecting Groups in Organic Synthesis", supra. Commonly used protecting groups for amines include benzyloxycarbonyl or alkoxycarbonyl (such as t-butyloxycarbonyl), trifluoroacetamide, fluorenylmethoxy carbonyl and formamide. Hydroxy groups may be protected by conversion to alkyl or aromatic esters, for example by reaction with an alkanoyl chloride such as acetyl chloride. Alternatively, hydroxy groups may be converted to ethers, for example alkyl or benzyl ethers. Carboxylic acid groups are often protected by esterification to an alkyl or aromatic ester.

The method of the invention is especially suitable for the deprotection of $^{18}$F-labelled mono- or polyhydroxy compounds, for example sugars, protected with alkanoate groups, in particular acetate.

The method of the invention is suitable for the synthesis of any $^{18}$F-labelled compound but is particularly well adapted for the production of PET tracers. The term "PET tracer" refers to a compound that can be detected by PET following administration to a subject. PET tracers are designed such that they are specifically taken up at the site of a particular physiology or pathophysiology, permitting an image of the physiology or pathophysiology to be created.

Therefore, in a second aspect of the invention there is provided a method for the synthesis of an $^{18}$F-labelled PET tracer compound, comprising the steps of:

(i) deprotection of a protected $^{18}$F-labelled PET tracer compound using a deprotection agent comprising a weak acid; and (ii) neutralisation and buffering of the product of step (i) by addition of a neutralisation agent, wherein buffering is between pH 4.5 and 8.0.

Examples of PET tracers which may be synthesised by the method of this aspect of the present invention include [$^{18}$F]-fluorodeoxyglucose ([$^{18}$F]-FDG), [$^{18}$F]-fluorodihydroxyphenylalanine ([$^{18}$F]-F-DOPA), [$^{18}$F]-fluorouracil, [$^{18}$F]-1-amino-3-fluorocyclobutane-1-carboxylic acid ([$^{18}$F]-FACBC), [$^{18}$F]-altanserine, [$^{18}$F]-fluorodopamine, 3'-deoxy-3'-$^{18}$F-fluorothymidine [$^{18}$F-FLT] and [$^{18}$F]-fluorobenzothiazoles. The structures of protected $^{18}$F-labelled compounds corresponding to these suitable PET tracers are shown below, labelled with the name of the PET tracer (wherein $p^1$ to $p^4$ are each independently a protecting group):

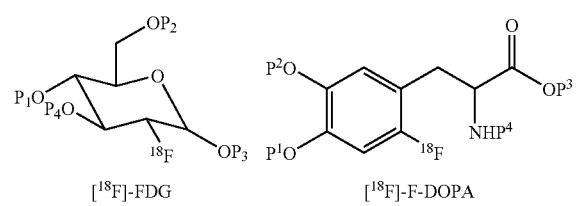

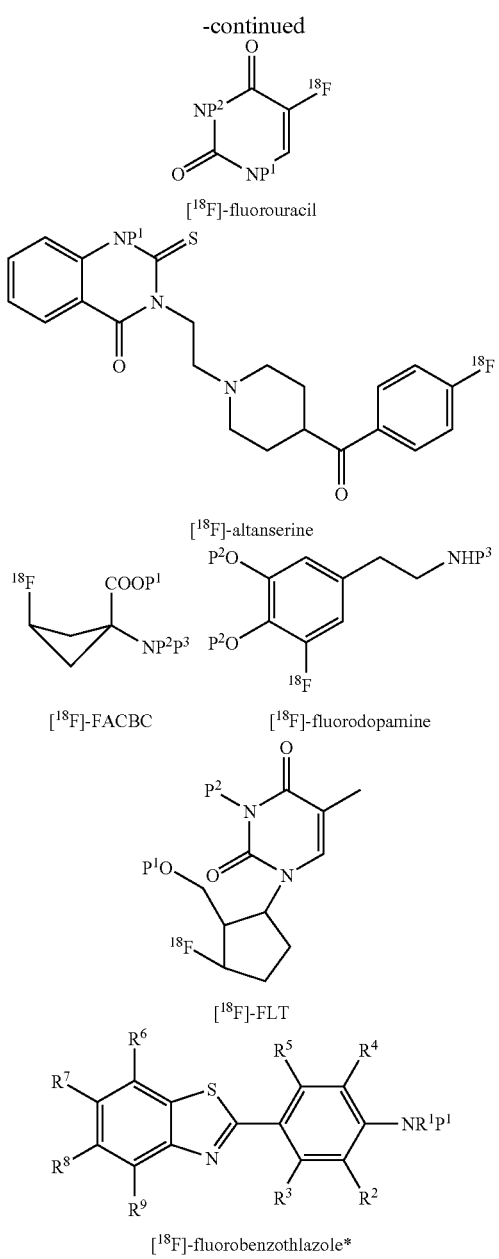

*$R^1$ is selected from hydrogen, $C_{1-6}$ alkyl, $C_{1-6}$ hydroxyalkyl, and $C_{1-6}$ haloalkyl; $R^2$ to $R^9$ are independently selected from hydrogen, halo, $C_{1-6}$ alkyl, $C_{1-6}$ haloalkyl, $C_{1-6}$ hydroxyalkyl, $C_{1-6}$ alkoxy, $C_{1-6}$ haloalkoxy, hydroxy, cyano, and nitro.

A particularly preferred PET tracer which can be synthesised by the method of the present invention is [$^{18}$F]-FDG.

Therefore in a further aspect of the invention, there is provided a method for the synthesis of [$^{18}$F]-FDG comprising the steps of:

(i) deprotection of a protected [$^{18}$F]-FDG to give [$^{18}$F]-FDG using a deprotection agent comprising a weak acid; and (ii) neutralisation and buffering of the product of the [$^{18}$F]-FDG from step (i) by addition of a neutralisation agent, wherein buffering is between pH 4.5 and 8.0.

In this aspect of the invention, it is preferred that buffering is to a pH of between 4.5 and 6.5 since at pH values higher than this there is significant epimerisation of the glucose to form mannose during terminal sterilisation.

It is particularly preferred that the protected starting material is tetra-acetyl[$^{18}$F]-fluorodeoxyglucose ([$^{18}$F]-FTAG).

When the product of the process is [$^{18}$F]-FDG, the protected [$^{18}$F]-FDG may be prepared by the initial step of reacting a protected derivative of mannose with an $^{18}$F-fluorinating agent. The mannose derivative will be derivatised with a leaving group such as trifluoromethane sulfonate (triflate) and the protecting groups are as set out above. A particularly suitable material from which to prepare the protected [$^{18}$F]-FDG is tetraacetyl mannose triflate.

Examples of weak acids that are suitable for use in the methods of the present invention include phosphoric acid, citric acid and acetic acid. The pKa values and buffering ranges of these weak acids are presented in Table I below:

TABLE I

| pKa and buffering ranges of selected weak acids | |
|---|---|
| Weak Acid | pKa |
| Phosphoric acid | 2.1 |
|  | 7.2 |
|  | 12.3 |
| Citric acid | 3.1 |
|  | 4.8 |
|  | 9.2 |
| Acetic acid | 4.7 |

Weak acids having more than one acidic hydrogen atom, for example phosphoric and citric acids (which each have three acidic hydrogen atoms), are preferred for use in the present invention. The reason for this is that the multiple pKa values mean that these acids are capable both of acting as a deprotecting agent and of forming a buffer system.

A most preferred weak acid of the present invention is phosphoric acid. Its first pKa value of 2.1 means that it is capable of hydrolytically removing the protecting group. The addition of the neutralising agent leads to the formation of a phosphoric acid/phosphate buffer system which maintains the pH of the solution within the desired range.

The deprotection agent may be a solution of the weak acid in an aqueous solvent or, alternatively, it may also comprise an additional acid component, for example a strong acid such as hydrochloric acid.

Where the weak acid is phosphoric acid, the deprotection agent may be a solution of phosphoric acid in HCl, preferably at a concentration of about 2M. Alternatively, the deprotection agent may be an aqueous solution of phosphoric acid. In either case, the phosphoric acid is suitably present in a concentration of between 10 mM (1.36 g/L) and 5M (680 g/L). Preferably, the molar range of phosphoric acid is between 1M and 4M, with between 3M and 4M being most preferred.

It is preferred that buffering to counteract the error in dispensing of acid and alkali is achieved within a pH range of 4.5 and 6.5. This range is preferred in particular when the $^{18}$F-labelled compound is [$^{18}$F]-FDG because it is known that at higher pH values generation of the additional product fluorodeoxymannose (FDM) occurs during the autoclaving process.

Depending on the protecting groups in question, deprotection is carried out at temperatures of between room temperature and 145° C. for up to 10 minutes. The skilled person will know that, for any particular deprotection protocol, it is preferred to carry out the reaction as close to room temperature as possible and for as short a time as possible.

The method of the invention can further comprise the steps of:

(iii) removal of organic solvent; and/or (iv) formulation of the $^{18}$F-labelled compound as an aqueous solution; and/or (v) sterilisation of the aqueous solution of step (iv).

These further steps are carried out in particular where the $^{18}$F-labelled compound is to be prepared into a pharmaceutically acceptable form, such as when the $^{18}$F-labelled compound is to be used as a PET tracer. The method of the present invention is particularly well adapted to automation, because the use of a weak acid, which can form part of a buffering system, means that errors in dispensing the reagents do not have too significant an effect on the pH of the product solution. In addition, problems with the solubility of buffers such as phosphate in alkaline solution do not occur.

In a preferred embodiment, the $^{18}$F-labelled compound is synthesised by means of an automated liquid-phase process. This is particularly appropriate when the $^{18}$F-labelled compound is a PET tracer and, indeed automated liquid-phase processes for the production of PET tracers are well known in the art. For example, [$^{18}$F]-FDG synthesis may be carried out with ease by means of either the Tracerlab FX Synthesiser (GE Healthcare, Little Chalfont, England) or the Tracerlab MX Synthesiser (GE Healthcare, Little Chalfont, England). For both systems, reagents are loaded onto the machine prior to starting the synthesis, which is then commenced by introducing $^{18}$F$^-$ directly from an [$^{18}$O]—H$_2$O target, under direct software control. In the case of the Tracerlab MX, loading of the reagents is achieved simply by means of attaching a disposable cassette to the machine. These disposable cassettes comprise various cartridges and reagent-containing vials and are designed to be suitable as a consumable item for use in conjunction with an automated process for the production of [$^{18}$F]-FDG. One means for carrying out the method of the invention might therefore be to incorporate the weak acid and the neutralisation agent into such a cassette for the deprotection, neutralisation and buffering steps of the synthesis. It is also envisaged that synthesis of the $^{18}$F-labelled compound by an automated liquid-phase process may be carried out using a microfluidic process on a microfluidic device. A number of advantages are forseen in relation to the use of microfluidic techniques. High throughput is made possible due to the ability to process several assays in parallel. Only small volumes of samples and reagents are required, resulting in small amounts of waste, which can often be contained in the device. All steps of the synthesis can be incorporated onto one device making complex processes simpler to perform. Furthermore, the cost of production for plastic microfluidic devices can be very low such that they can be disposable. Further detail on the performance and application of microfluidic techniques in drug development can be found in a review by Bernhard et al [Advanced Drug Delivery Reviews, Volume 55, Issue 3, 24 February 2003, Pages 349-377].

In an alternative preferred embodiment, the protected $^{18}$F-labelled compound may be obtained in a solid-phase reaction. Most preferably, the protected $^{18}$F-labelled compound is released into the solution phase upon radiofluorination. WO 03/002157 describes solid-phase processes for producing $^{18}$F-labelled compounds quickly and with high specific activity yet avoiding time-consuming purification steps, such that the resultant $^{18}$F-labelled compound is suitable for use as a PET tracer. It is also envisaged that release of the compound from the solid phase can alternatively take place upon deprotection resulting in release of the deprotected $^{18}$F-labelled compound. These solid-phase methods also lend themselves to automation with advantages of ease of production and greater throughput.

EXAMPLES

Example 1

Figure 1:
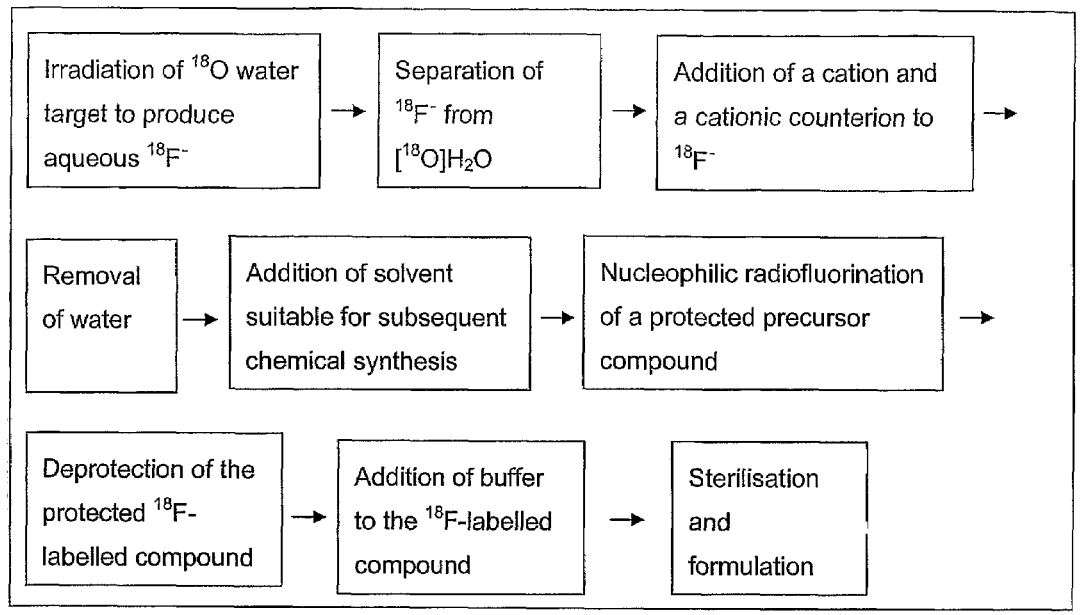
FIG. 1 is a flow diagram of the main steps typically carried out in the synthesis of an $^{18}$F-labelled compound.

Analysis of the Buffering Capacity of Phosphoric Acid on HCl Deprotected FDG Neutralised by NaOH This example describes the experiment used to analyse the buffering capacity of phosphoric acid on HCl-deprotected FDG neutralised by NaOH.

A 16 µl aliquot of 0.15 g/ml of the protected precursor compound, tetraacetyl [$^{18}$F]-FDG, in acetonitrile was added to a glassy carbon reaction vessel. This was heated to constant mass at 50° C. leaving 2.4 mg PFDG in the vessel. The vessel was sealed and pressure tested with approximately 2 bar of air. 2.5 ml of a 5M solution of HCl and 294 µl of 85% phosphoric acid was added and the vessel was heated to 145° C. for 15 minutes and then cooled. 0.5 ml of the reaction mixture was removed from the vessel and titrated against 1M NaOH.

Titration of the HCl deprotected reaction mixture against 1M NaOH revealed that the phosphate retains the pH within the range 4.5 to 6.3 from 1.47 ml to 1.63 ml NaOH.

Example 2

Deprotection of Protected FDG with 525 mg/ml Phosphoric Acid

This example describes the deprotection of protected FDG with 525 mg/ml phosphoric acid.

A 16 µl aliquot of 0.18 g/ml of the protected precursor compound, tetraacetyl [$^{18}$F]-FDG, in acetonitrile was added to a glassy carbon reaction vessel. This was heated to constant mass at 50° C. leaving 2.8 mg pFDG in the vessel. The vessel was sealed and pressure tested with approximately 2 bar of air. 2 ml of a solution of 525 mg/ml phosphoric acid in HPLC grade water was added to the reaction vessel and heated to 145° C. and held at this temperature for 10 minutes and then cooled.

A portion was removed and titrated to approximately pH 8.0 with 5M NaOH.

HPLC analysis using 0.1M NaOH mobile phase at 1 ml/min and electrochemical detection (ECD) was carried out on (i) standard FDG solution, (ii) the final reaction mixture and (iii) co-injection of (i) and (ii).

No precipitation was observed after the deprotection reaction. HPLC analysis revealed that the main peak in the final reaction mixture was FDG, indicating that the deprotection was successful.

Example 3

Deprotection of Protected FDG with 525 mg/ml phosphoric acid in 2M HCl

This example describes the deprotection of protected FDG with 525 mg/ml phosphoric acid in 2M HCl. A 16 μl aliquot of 0.11 g/ml of the protected precursor compound, tetraacetyl [$^{18}$F]-FDG, in acetonitrile was added to a glassy carbon reaction vessel. This was heated to constant mass at 50° C. leaving 1.8 mg protected FDG in the vessel. The vessel was sealed and pressure tested with approximately 2 bar of air. 2 ml of a solution of 525 mg/ml phosphoric acid in 2M HCl was added to the reaction vessel and heated to 145° C. and held at this temperature for 10 minutes and then cooled.

A portion was removed and titrated to approximately pH 8.0 with 5M NaOH. HPLC analysis using 0.1M NaOH mobile phase at 1 ml/min and ECD detection was carried out on (i) standard FDG solution, (ii) the final reaction mixture and (iii) co-injection of (i) and (ii).

No precipitation was observed after the deprotection reaction. HPLC analysis revealed that the main peak in the final reaction mixture was FDG, indicating that the deprotection was successful.

Example 4

Titration of Phosphoric Acid with Sodium Hydroxide to Determine pKa Value

Figure 2:
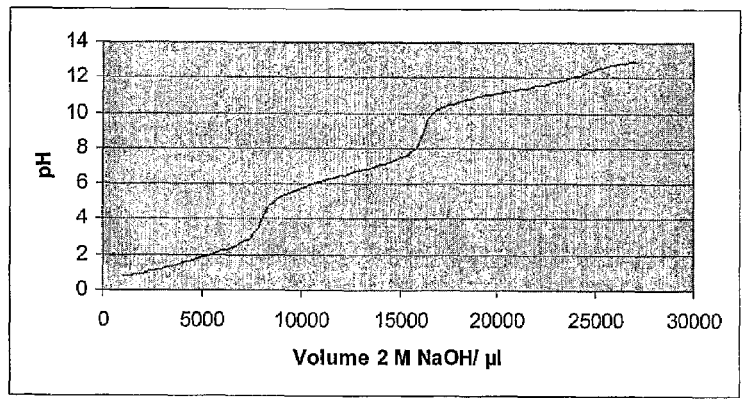
FIG. 2 is a plot showing the pH of the solution when 525 mg/ml phosphoric acid in water was titrated against 2M sodium hydroxide. The second point of inflection of the curve occurs at about pH 6.5.

A solution of 525 mg/mi phosphoric acid in water was titrated against 2M sodium hydroxide in order to determine the effective pKa value for this system. The titration curve is shown in FIG. 2, from which it can be seen that under these conditions, the second pKa value was about 6.5. This indicates that, under these experimental conditions, the phosphoric acid/phosphate buffer is suitable for maintaining the pH of a solution at between about pH5.5 and pH7.5. The phosphoric acid/phosphate buffer system is therefore well suited for use in the deprotection of protected $^{18}$F-labelled compounds.

The invention claimed is:

1. A method for the synthesis of an $^{18}$F-labelled mono- or polyhydroxy compound comprising the following steps:
    (i) deprotection of an alkanoate-protected $^{18}$F-labelled compound corresponding to the $^{18}$F-labelled mono- or polyhydroxy compound using a deprotection agent comprising a weak acid said weak acid having a pKa of 2 or more; and,
    (ii) neutralisation and buffering of the product of step (i) by addition of a neutralisation agent, wherein buffering is between pH 4.5 and 8.0.

2. A method as claimed in claim 1 wherein said protected $^{18}$F-labelled compound is an $^{18}$F-labelled PET tracer compound and said alkanoate-protected $^{18}$F-labelled compound corresponding to the $^{18}$F-labelled mono- or polyhydroxy compound is an alkanoate-protected $^{18}$F-labelled mono- or polyhydroxy PET tracer compound.

3. A method as claimed in claim 2, wherein the PET tracer is [$^{18}$F]-fluorodeoxyglucose ([$^{18}$F]-FDG).

4. A method as claimed in claim 3, wherein the alkanoate-protected $^{18}$F-labelled PET tracer has the following structure, wherein $P^1$ to $P^4$ are each independently a protecting group:

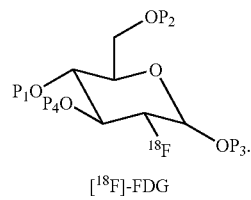

[$^{18}$F]-FDG

5. A method as claimed in claim 4, wherein the protected [$^{18}$F]-FDG is prepared by reacting a protected derivative of mannose with an $^{18}$F-fluorinating agent.

6. A method as claimed in claim 4, wherein the protected [$^{18}$F]-FDG is tetraacetyl [$^{18}$F]-FDG.

7. A method as claimed in claim 5, wherein the protected derivative of mannose is tetraacetyl mannose trifluoromethane sulfonate.

8. A method as claimed in claim 1, wherein the neutralising agent is sodium hydroxide.

9. A method as claimed in claim 1, wherein the deprotection agent is a solution of the weak acid in an aqueous solvent.

10. A method as claimed in claim 1, wherein the weak acid is phosphoric acid, citric acid or acetic acid.

11. A method as claimed in claim 10, wherein the weak acid is phosphoric acid.

12. A method as claimed in claim 11, wherein the concentration of phosphoric acid is from 10 mM to 5M.

13. A method as claimed in claim 12, wherein the concentration of phosphoric acid is from 3M to 4M.

14. A method as claimed in claim 1, wherein the deprotection agent further comprises a strong acid.

15. A method as claimed in claim 14, wherein the strong acid is hydrochloric acid.

16. A method as claimed in claim 1, wherein the buffering is within a pH range of 4.5 and 6.5.

17. A method as claimed in claim 1, wherein the deprotection is carried out at temperatures of between room temperature and 145° C. for up to 10 minutes.

18. A method as claimed in claim 1 further comprising the steps of:
    (iii) removal of organic solvent; and/or
    (iv) formulation of the $^{18}$F-labelled compound as an aqueous solution; and/or
    (v) sterilisation of the aqueous solution of step (iv).

19. A method as claimed in claim 1 which is automated.

20. A method as claimed in claim 19 which is an automated liquid-phase process.

21. A method as claimed in claim 20 wherein the automated liquid-phase process is a microfluidics process.

22. A method as claimed in claim 19 wherein the protected $^{18}$F-labelled compound is obtained in a solid-phase reaction.

23. A method as claimed in claim 22 wherein the protected $^{18}$F-labelled compound is released into solution phase from a solid phase upon radiofluorination.

24. A method as claimed in claim 22 wherein the protected $^{18}$F-labelled compound is released into solution phase from a solid phase upon deprotection.

* * * * *